(12) United States Patent
Lomax et al.

(10) Patent No.: US 7,920,675 B2
(45) Date of Patent: Apr. 5, 2011

(54) PRODUCING A RADIATION TREATMENT PLAN

(75) Inventors: Antony Lomax, Windisch (CH); Cezarina Negreanu-Macian, Winterthur (CH)

(73) Assignee: Siemens Aktiengesellschaft, München (DE)

( * ) Notice: Subject to any disclaimer, the term of this patent is extended or adjusted under 35 U.S.C. 154(b) by 0 days.

(21) Appl. No.: 12/419,017

(22) Filed: Apr. 6, 2009

(65) Prior Publication Data

US 2009/0304154 A1 Dec. 10, 2009

(30) Foreign Application Priority Data

Apr. 10, 2008 (DE) .................... 10 2008 018 417

(51) Int. Cl.
*A61N 5/10* (2006.01)
(52) U.S. Cl. ........................................................ 378/65
(58) Field of Classification Search .................. 378/62, 378/64, 65
See application file for complete search history.

(56) References Cited

U.S. PATENT DOCUMENTS

| 2006/0285640 | A1 | 12/2006 | Nizin et al. |
| 2007/0003011 | A1 | 1/2007 | Lane |

FOREIGN PATENT DOCUMENTS

WO WO 2008/016795 2/2008

OTHER PUBLICATIONS

German Office Action dated Dec. 2, 2008 with English translation.
European Patent Office Communication dated Apr. 2009 with English translation.
Abstract ID: 7798 Factors Affecting the Selection of Beam Directions in Proton Therapy.
Martijn Engelsman et al., "Impact of Simple Tissue Inhomogeneity Correction Algorithms on Conformal Radiotherapy of Lung Tumors," *Radiotherapy and Oncology* 60 (2001), pp. 299-309.
Jäkel et al., "Treatment Planning for Heavy Ion Irradiation," *Physica Medica*, ol. XIV, Supplement 1, Jul. 1998, pp. 53-62.
Jin et al., "Investigation of Optimal Beam Margins for Stereotactic Radiotherapy of Lung-Cancer Using Monte Carlo Dose Calculations," *Phys. Med. Biol.* 52 (2007), pp. 3549-3561.
Carol McGibney et al., Analysis of Dose Distribution in the 'Rind'—A Volume Outside the PTV—in 3-Dimensional Conformal Radiation Therapy of Non-Small Cell Lung Cancer, *Radiotherapy and Oncology* 66 (2003), pp. 87-93.
R.C. Miller et al., "Impact of Beam Energy and Field Margin on Penumbra at Lung Tumor-Lung Parenchyma Interfaces," Int. J. Radiat. Oncol. Biol. Phys., vol. 41, No. 3, 1998, pp. 707-713.

(Continued)

*Primary Examiner* — Irakli Kiknadze
(74) *Attorney, Agent, or Firm* — Brinks Hofer Gilson & Lione

(57) ABSTRACT

The present embodiments relate to producing a radiation treatment plan. In one embodiment, the method may include specifying a dataset in which an object requiring to be irradiated is represented; determining a target volume requiring to be irradiated within the object; ascertaining a metric identifying a density heterogeneity for a region that will be struck by the planned treatment beam; and determining as a function of the ascertained metric a safety margin for the target volume requiring to be irradiated.

15 Claims, 3 Drawing Sheets

OTHER PUBLICATIONS

D. Pflugfelder et al., Quantifying Lateral Tissue Heterogeneities in Hadron Therapy; *Med. Phys.* 34(4) Apr. 2007, Am. Assoc. Phys. Med., pp. 1506-1513.

Rietzel et al., "Four-Dimensional Image-Based Treatment Planning: Target Volume Segmentation and Dose Calculation in the Presence of Respiratory Motion," *International Journal of Radiation: Oncology Biology Physics*, vol. 61, No. 55, 2005, pp. 1535-1550.

Y. Yang et al., "Towards Biologically Conformal Radiation Therapy (BCRT) Selective IMRT Dose Escalation Under the Guidance of Spatial Biology Distribution," Med. Phys. 32(6), Jun. 2005, Am. Assoc. Phys. Med., p. 1473-1484.

PRODUCING A RADIATION TREATMENT PLAN

This patent document claims the benefit of DE 10 2008 018 417.9, filed Apr. 10, 2008, which is hereby incorporated by reference.

BACKGROUND

The present embodiments relate to producing a radiation treatment plan as part of planning the irradiating of diseased tissue with a treatment beam.

Radiation therapy is among the established methods employed in the treatment of tumorous diseases. Radiation therapy entails directing beams onto a target volume within a body. The target volume may be irradiated. Within the scope of particle therapy, which is a particular form of radiation therapy, for example, protons, carbon ions, and other ions are accelerated to high energies and directed onto the tissue requiring to be irradiated. However, other types of beams, for example, electron beams and x-rays, can be used for irradiation. Irradiating methods, which are used in radiation or particle therapy, may be used in non-therapeutic domains. The non-therapeutic domains include, for example, research conducted within the scope of particle therapy on non-living phantoms or bodies and the irradiating of materials.

To irradiate a target volume as accurately as possible, the treatment beam should deliver energy only within the target volume. Surrounding tissue should be spared. To achieve delivery of energy only within the target volume, a radiation treatment plan precisely defining the parameters based on which irradiating is to take place is usually produced before a target volume is irradiated.

Owing to various factors it may not be possible to precisely plan and predict the irradiating of a target volume in every detail. The irradiation can deviate slightly from the ideal irradiating that has been planned. Reasons for the deviation include moving of the target volume, lack of precision in the target volume's positioning relative to the treatment beam, lack of precision during planning, and changes occurring within the target volume between planning and treatment.

Attempts are made to take the lack of precision and imponderables into account during planning so that as good as possible irradiating results. For example, a safety margin around the target volume may be set so that it will always be irradiated adequately.

The conference paper titled "Factors affecting the selection of beam directions in proton therapy", Lomax T, 44$^{th}$ AAPM Annual Meeting, Montréal, July 2002, Abstract ID 7798, discloses that an index by which density heterogeneities are quantified is able to predict the magnitude of effects that can impair a treatment plan.

The publication by Pflugfelder D et al. titled "Quantifying lateral tissue heterogeneities in hadron therapy", Medical Physics, 2007, 34(4), 1506-1513, discloses a method for quantifying lateral tissue heterogeneities in a scanned particle beam. Applied particle beams are each individually rated by an index and the multiplicity of indices employed in optimizing irradiation planning.

SUMMARY AND DESCRIPTION

The present embodiments may obviate one or more of the drawbacks or limitations inherent in the related art. For example, in one embodiment, a radiation treatment plan may be produced that is robust with respect to lack of precision, will make actual irradiating possible that substantially conforms to the radiation treatment plan, and at the same time can be determined with favorable computational overhead.

In one aspect, a method for producing a radiation treatment plan includes specifying a dataset in which an object requiring to be irradiated is represented, determining a target volume requiring to be irradiated within the object, ascertaining a metric identifying a density heterogeneity for a region that will be struck by the planned treatment beam, and determining as a function of the ascertained metric a safety margin for the target volume requiring to be irradiated.

In a second aspect, a system for producing a radiation treatment plan is provided. The system has a computer unit, an input device, and an output device. The system is embodied for implementing the method set forth in the first aspect or a different method.

A radiation treatment plan can then be produced based on the safety margin that has been determined as a function of the ascertained metric.

The dataset, which may be a computed tomography (CT) dataset, images the object requiring to be irradiated usually three-dimensionally. The dataset forms the basis for ensuing irradiation planning. The target volume interactively irradiated by a user. The interactive irradiation may be done manually, semi-automatically, or automatically, for example, with the aid of known segmenting algorithms.

The metric is then ascertained for a planned treatment beam. Ascertaining the metric is done with the aid of the data stored in the dataset. The metric may be an index that rates the density heterogeneity in a region that would be struck by the planned treatment beam.

The metric is then used in determining the safety margin for the target volume requiring to be irradiated. The greater the heterogeneity of the region struck by the treatment beam, the greater will be the degree of uncertainty with which the tissue requiring to be irradiated will be subjected to a dose from a planned treatment beam. The density heterogeneity in the area struck by the treatment beam will influence the homogeneity of the target dose within the target volume, the coverage of the target volume with the dose that is deposited, and/or the sensitivity of a dose distribution toward a lack of spatial positional certainty of the target volume. Those effects will influence the choice of safety margin around the target volume.

The safety margin, for example, the size, width, and/or extent, is then selected as a function of the metric. The above-cited effects will be taken into account automatically. The greater, for example, the degree of uncertainty is with which the target volume will actually be subjected to a dose, owing to a high density heterogeneity, the greater the safety margin, for example, can be selected from the start during irradiation planning for ensuring that the target volume will always be subjected to a desired minimum dose.

In one embodiment, the metric for the entire area that would be struck by the treatment beam may be ascertained. In other words, a single metric will rate the density heterogeneity in the entire area.

In another embodiment, only parts (portions) of the entire area may be taken into account. For example, the metric may be ascertained for the region situated in front of the target volume in the beam direction, meaning in the incidence channel in front of the target volume. As a result, if variations in the homogeneity of the deposited dose in the center of the target volume are regarded as less relevant, then just the boundary regions of the area struck by the treatment beam can be rated in terms of their density heterogeneity when the metric is ascertained.

Especially in the case of scanning methods that employ a particle beam and where the dose requiring to be deposited is achieved by a multiplicity of individual particle beams (what are termed "beamlets") that are to be applied successively, the region whose density heterogeneity is identified by the metric can include an area that will be struck by at least a plurality of the particle beams requiring to be applied successively. Accordingly, it is not the heterogeneity within the area of each individual particle beam that will be rated but the heterogeneity within a larger area. This is advantageous because a multiplicity of heterogeneity indices separately rating the heterogeneity in each individual beamlet's target area will mean a high level of computing overhead over the further course of producing and/or optimizing the radiation treatment plan.

The metric may be used for determining or optimizing an angle at which the treatment beam enters the target volume. For example, a specific entry angle of the treatment beam may be rejected if the associated metric that rates the density heterogeneity exceeds a specific threshold.

The method may include checking. A dose distribution required by the planned treatment beam may be checked for the dose distributions robustness with respect to incorrect irradiating. In other words, the dose distribution is checked with respect to spatial imprecision in depositing the desired radiation dose. The irradiation planning may, where applicable, be changed. Accordingly, a radiation treatment plan that is not sufficiently robust with respect to the type of imprecision may be determined. On the occurrence of such imprecision, the dose actually deposited will deviate too greatly from the desired radiation dose. Accordingly, the radiation treatment plan may be changed, for example, by choosing a different safety margin, by changing the angle of incidence, or by continuing to make other changes until the radiation treatment plan is sufficiently robust with respect to spatial imprecision in dose depositing. Imprecision will result only in a slightly changed dose distribution whose deviation from a desired radiation dose can be tolerated.

The measures described can be applied to different scanning methods employing a particle beam.

For example, in one embodiment, the measures may be applied to a spot scanning method. The spot scanning method may keep the particle beam on each target point for a specific length of time and/or deposits a pre-specified number of particles at each target point, then is switched off while deflection magnets are set for directing the particle beam at a next target point. In another example, a raster scanning method is used. With the raster scanning method, the particle beam stays on each target point for a pre-specified period or deposits a pre-specified number of particles at each target point but is not or not always switched off between the target points.

With what are termed continuous scanning methods, the target points form coherent lines, meaning they form continuous (or quasi-continuous) quantities, with their number being countably infinite. The particle beam is continuously deflected at least within one line or row into an iso-energy layer and traverses the target points without stopping at any single location. With a depth modulation device, a continuous scanning method is provided. The penetration depth of the particle beam is continuously modulated using the continuous scanning method.

In a third aspect, a method for producing a radiation treatment plan comprises specifying a dataset in which an object requiring to be irradiated is represented, determining a target volume requiring to be irradiated within the object, specifying at least two irradiation fields with which the target volume will be irradiated from in each case a different direction, ascertaining for each irradiation field a metric that identifies a density homogeneity for a region which will be struck during planned irradiating with the respective irradiating field, and determining a weighting for the at least two irradiating fields as a function of the metrics ascertained.

In a fourth aspect, a device for producing a radiation treatment plan is provided. The device includes a computer unit, an input device, and an output device and is embodied for implementing the method according to the third aspect.

A radiation treatment plan may be produced based on the weighting that has been determined as a function of the metric ascertained.

The radiation treatment plan may be produced using at least two irradiation fields, for example, using a treatment beam directed at the target volume in each case from a different direction. As a result, a desired dose may be achieved within the target volume while at the same time omitting areas that are not to be irradiated.

With the two irradiation fields, different regions within the object will be struck by the treatment beam. For each of the irradiation fields, a metric is then ascertained which rates the density heterogeneity in the respective region struck by the treatment beam. The metrics ascertained are then used for determining a weighting for the irradiation fields among each other. If, for example, a first irradiation field has a metric identified by a high density heterogeneity and a second irradiation field has a metric identified by a low density heterogeneity, that can be taken into account in determining the weighting for the two irradiation fields. The irradiation field having the high density heterogeneity may be assigned a lesser weighting. As a result, the degrees of uncertainty arising while the irradiation field having the high density heterogeneity is being irradiated can be reduced.

Determining the weighting among a plurality of irradiation fields in keeping with that method does not preclude planning. For example, further irradiation fields whose weighting is not established using the heterogeneity metric may be used. The weighting for the further irradiation fields may, for example, be predefined, or variables other than the heterogeneity metric may be used for ascertaining the weighting.

In one embodiment, when the metric is being ascertained for one of the irradiation fields, it is possible, for example, to ascertain the metric for the entire area that would be struck by the irradiation field's treatment beam. As a result, a single metric will rate the heterogeneity in the entire area.

In another embodiment, only parts of the entire area may be rated with the metric. For example, in the case of one irradiation field, the metric can be ascertained for the region situated in front of the target volume in the beam direction, for example, in the incidence channel in front of the target volume. When variations in the homogeneity of the deposited dose in the center of the target volume are regarded as less relevant, then just the boundary regions of the area struck by the treatment beam can be rated in terms of their density heterogeneity when the metric is ascertained.

The method may be followed by checking. A radiation treatment plan that has been produced or an irradiation field that has been planned may be checked for its robustness with respect to incorrect irradiating due to spatial imprecision in depositing the desired radiation dose and, where applicable, then be changed. It may be determined, for example, that a radiation treatment plan or irradiation field is not sufficiently robust with respect to the type of imprecision. On the occurrence of such imprecision, the dose actually deposited will deviate too greatly from the desired radiation dose or its distribution. Accordingly, the radiation treatment plan or irradiation field can be changed, for example, by choosing a different safety margin, by changing the angle of incidence, or by continuing to make other changes until the radiation treatment plan or irradiation field is sufficiently robust with respect to spatial imprecision in dose depositing. Spatial imprecision will result only in a slightly changed dose distribution whose deviation from a desired radiation dose or distribution can be tolerated.

Especially in the case of scanning methods that employ a particle beam and where the dose requiring to be deposited is achieved by a multiplicity of individual particle beams (what are termed "beamlets") that are applied successively from the same direction to different target points within the target volume, the region whose density heterogeneity is identified by the metric for one of the irradiation fields includes an area that will be struck by at least a plurality of the particle beams being applied successively. The area that will be struck may include the area that will be struck by all the particle beams requiring to be applied successively for an irradiation field. The heterogeneity within each individual particle beam's area may not be rated. Instead, the heterogeneity within a larger area may be rated. That is the basis of the advantages explained above.

Once a radiation treatment plan has been produced, methods to ascertain control parameters for controlling the irradiation system in keeping with the radiation treatment plan may be developed. The irradiation system may be controlled with the ascertained control parameters for irradiating an object for which the radiation treatment plan has been produced in accordance with the plan.

In one embodiment, a device for determining control parameters of an irradiation system is provided. The device, based on the produced radiation treatment plan, ascertains the control parameters for controlling the irradiation system according to what is specified in the radiation treatment plan. The irradiation system, which is embodied for irradiating the object in accordance with the produced radiation treatment plan, for example, with the aid of the control parameters that have been ascertained by the device for determining control parameters. The irradiation system can include the device for producing a radiation treatment plan and/or the device for determining control parameters of an irradiation system.

DETAILED DESCRIPTION

Figure 1:
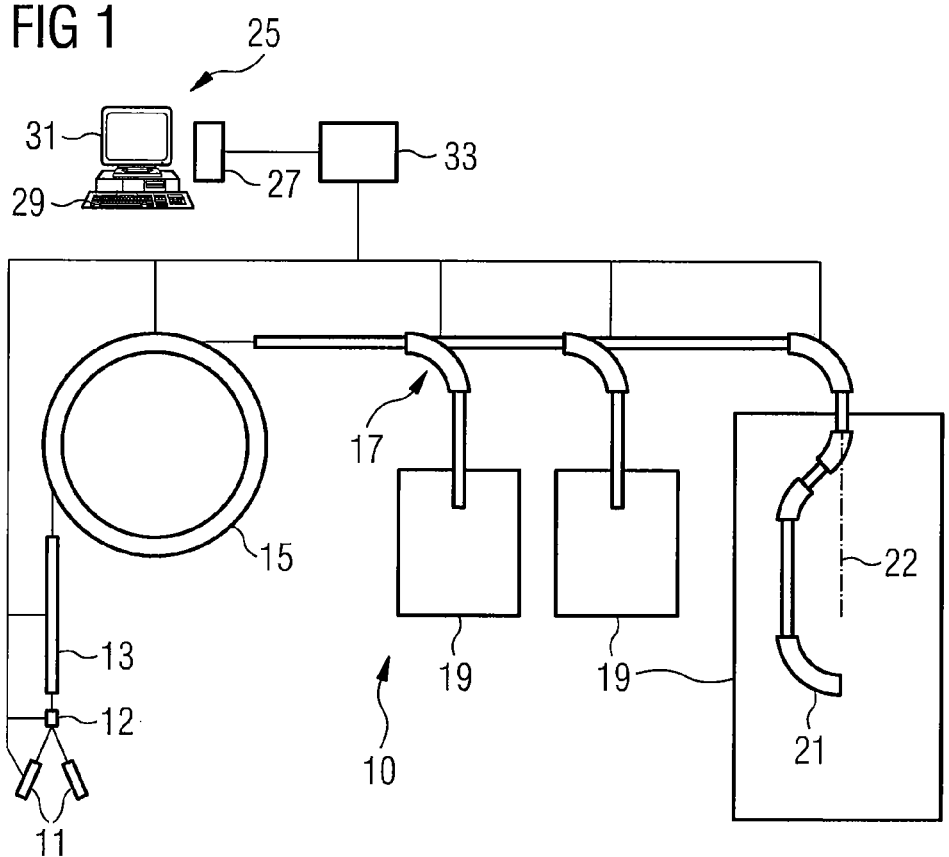
FIG. 1 illustrates one embodiment of a particle therapy system.

FIG. 1 illustrates a particle therapy system 10. The particle therapy system 10 may be used to irradiate body, such as tumor-diseased tissue, using a particle beam having particles.

The particles may be ions, such as protons, pions, helium ions, carbon ions, or other kinds of ions. Particles may be generated in a particle source 11. As shown in FIG. 1, there may be two particle sources 11 that generate two different kinds of ions. Accordingly, it is possible to change over between the two kinds of ions within a short interval of time. A switching magnet 12, for example, may be used for the switching. The switching magnet 12 is located between the ion sources 11 and a pre-accelerator 13. For example, the particle therapy system 10 may be operated simultaneously with protons and with carbon ions.

The ions that have been obtained from one or both of the ion sources 11 or selected by the switching magnet 12 are accelerated in the pre-accelerator 13 to a first energy level. The pre-accelerator 13 is may be a linear accelerator (LINAC: "LINear ACcelerator"). The particles are then fed into an accelerator 15, for example, a synchrotron or cyclotron. In the accelerator 15, the particles are accelerated to high energies of the kind necessary for irradiating. When the particles have left the accelerator 15, a high energy beam transport system 17 takes the particle beam to one or more treatment rooms 19. In a treatment room 19, the accelerated particles are directed onto a body requiring to be irradiated. Directing the particle onto a body may be done from a fixed direction (in what are termed fixed-beam rooms) or from different directions via a rotatable gantry 21 that can be moved around an axis 22.

A device 25 for producing a radiation treatment plan is customarily employed in a particle therapy system 10. The device 25 may include a computer unit 27 having an input device 29 and an output device 31 for interacting with a user. After a radiation treatment plan has been produced, a control device 33 for controlling the system can ascertain control parameters in keeping with the radiation treatment plan that has been produced and control the system accordingly. The device 25 for producing a radiation treatment plan may belong to the particle therapy system 10 or be embodied as a separate unit.

The structure of a particle therapy system 10 illustrated in FIG. 1 may also depart from what is shown.

The exemplary embodiments may be used in particle therapy systems of such or similar type or in medical systems generally.

Various irradiation fields/entire irradiating plans were tested in the production of irradiating plans. Testing involved rating each of the irradiation fields with a heterogeneity index that identifies the density heterogeneity "seen" by an irradiation field.

The density heterogeneity was identified by a single heterogeneity index for each irradiation field. The lower the heterogeneity index was, the higher the anatomy was through which the irradiation field passed, so the more homogeneous the anatomy was in an irradiation field's entry channel. The robustness of an irradiation field/radiation treatment plan was then tested by evaluating different error-dose distribution files. Error-dose distribution files are therein re-calculated dose distributions of an irradiation field/radiation treatment plan taking account of different degrees of uncertainty. All error-dose distributions were combined during robustness testing employing a standard probability distribution, with the resulting distribution then being analyzed in a two-fold manner. Rating was carried out a first time using what is termed the known gamma index used for rating a radiation treatment plan's quality, and a second time by comparing the D98 region (the region in which the deposited dose is at least 98% of the desired dose) with the target volume (deltaD98) requiring to be irradiated. Account was therein taken of coincidental spatial errors of 2 mm and 4 mm along with the effect due to a change in the safety margin of 2 mm to 5 mm. Systematic range-specific uncertainties of +/−3% were additionally included in the analysis.

Figure 2:
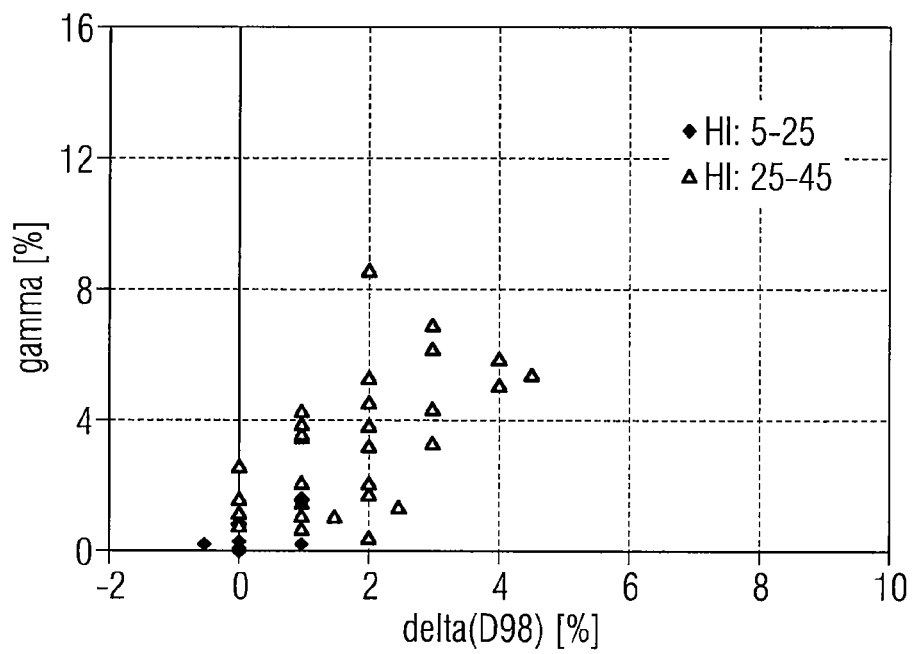
FIG. 2 illustrates one embodiment of different heterogeneity indices.

For different irradiation fields having different heterogeneity indices (HI), the gamma index that was ascertained (y axis) was plotted in the diagram in FIG. 2 against the deltaD98 value that was ascertained (x axis). Explained in more detail, what is plotted on the y axis is the percentage of target points of an irradiation field that have a gamma index>1 (acceptance criterion applied to calculating the gamma indices for the target points: 3%/3 mm).

Irradiation fields having an HI>25 are therein shown in the diagram having open, triangular symbols and irradiating plans having an HI<25 are shown in the diagram having closed, rhomboid symbols. Irradiation fields having a large HI have significantly higher gamma values and at the same time a slight shift toward higher deltaD98 values. Accordingly, density heterogeneities influence the dose stress to which the entire target volume is subjected, but to a lesser extent the coverage of the target volume. It has therein been recognized that a change in the safety margin will generally reduce the deltaD98 value but have a lesser influence on the gamma analysis.

The role of systematic and coincidental errors in the production of a radiation treatment plan may be ascertained by analysis methods. A greater safety margin may be selected in the case of irradiation fields having a high heterogeneity index in order to achieve sufficient coverage of the target volume (favorable deltaD98 value). For example, an irradiation field's angle of incidence onto the target volume may be selected such that there will be as small as possible a heterogeneity index for the resulting irradiation field. If a plurality of irradiation fields are employed in a radiation treatment plan, then the heterogeneity index may be employed in determining the individual irradiation fields' weighting. For example, the irradiation field having the larger heterogeneity index may be weighted lower than the irradiation field having the smaller heterogeneity index. The target volume can in that way be irradiated more accurately and with the surrounding tissue being better protected. A radiation treatment plan that is overall more robust with respect to uncertainty can consequently furthermore be obtained.

Figure 3:
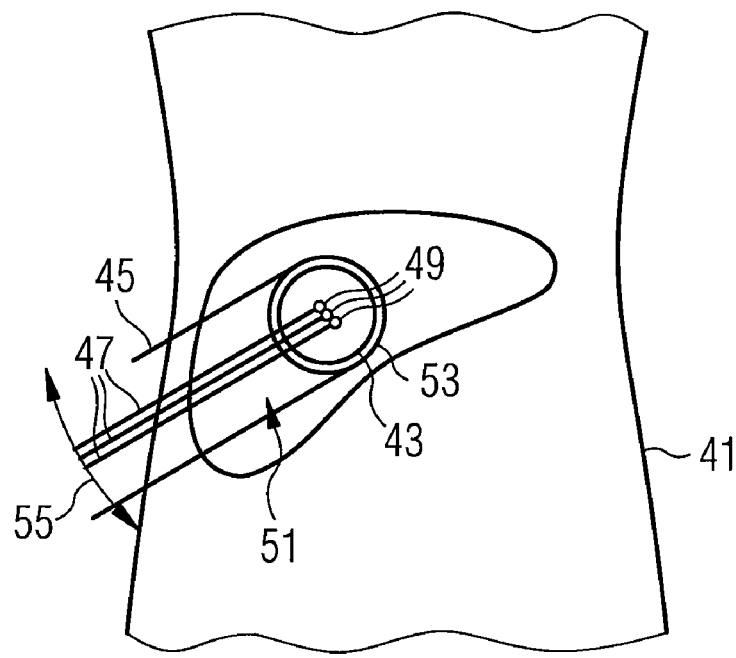
FIG. 3 illustrates a target volume to be irradiated with one planned irradiation field.

One embodiment of planning irradiating with an irradiation field is shown with reference to FIG. 3.

The representation of the object 41 to be irradiated or of the target volume 43 to be irradiated is based on a planning dataset obtained through, for example, computed tomography. The target volume 43 to be irradiated may be established in the object 41 requiring to be irradiated using an image that has been obtained from the planning dataset and is presented to a user.

An irradiation field 45 may be established with which the target volume 43 will be irradiated. One irradiation field 45 is defined by a selectable direction of incidence that establishes the direction from which the target volume 43 will be irradiated. When the target volume 43 is irradiated with particles within the scope of the scanning method, then the irradiation field is the total of a multiplicity of particle beams 47 (beamlets) to be applied one after the other from the same direction of incidence, which are successively directed at different target points 49 within the target volume 43. That is symbolized in FIG. 3 by a few target points 49 shown in the target volume 43.

The density heterogeneity in the case of an irradiation field 45 is defined principally by the density heterogeneity of the area 51 situated in the object 41 to be irradiated in front of the target volume 43 in the beam direction. If, for example, a different irradiation field is selected, then the density heterogeneity will change because a different anatomical area having a different density heterogeneity will be situated in front of the target volume 43.

Once the irradiation field 45 has been established, a metric is ascertained for the irradiation field 45 that identifies the density heterogeneity for the irradiation field 45. The metric may be ascertained for, for example, the entire area struck by the irradiation field 45, but also just for parts of the overall area. The metric may be determined just for the area 51 situated in front of the target volume in the beam direction, or just for areas situated in the irradiation field's boundary region. In contrast to known methods where the lateral density heterogeneity is ascertained for each individual particle beam 47 (beamlets) and included in irradiation planning, one metric is here determined for an area struck by a multiplicity of particle beams requiring to be applied one after the other.

The safety margin 53 is then selected as a function of the metric that has been ascertained. The angle of incidence of the irradiation field 45 can may be optimized likewise as a function of the metric, for example in such a way that an optimized angle of incidence will produce an irradiation field 45 having a low density heterogeneity. The angle of incidence that can be variably selected and optimized is symbolized by a curved double arrow 55.

The safety margin 53 and/or the angle of incidence may be selected by way of, for example, a functional correlation that is stored in a computer unit and is based on experimental values or relies on calculations. The calculations may include, for example, a radiation treatment plan's error proneness with respect to uncertainties during irradiating such as movement within the target volume and positional uncertainty. Alternatively, the safety margin's extent may be ascertained via, for example, an empirically ascertained, mathematical correlation as a function of the metric. The angle of incidence may, for example, be varied multiple times until an angle of incidence has been found at which the associated irradiation field has a favorable density heterogeneity.

The safety margin 53 and/or the angle of incidence are/is usually selected taking additional account of pre-specified boundary conditions, for example, taking account of omitting organs not intended to be stressed by a dose (what are termed "organs at risk").

Figure 4:
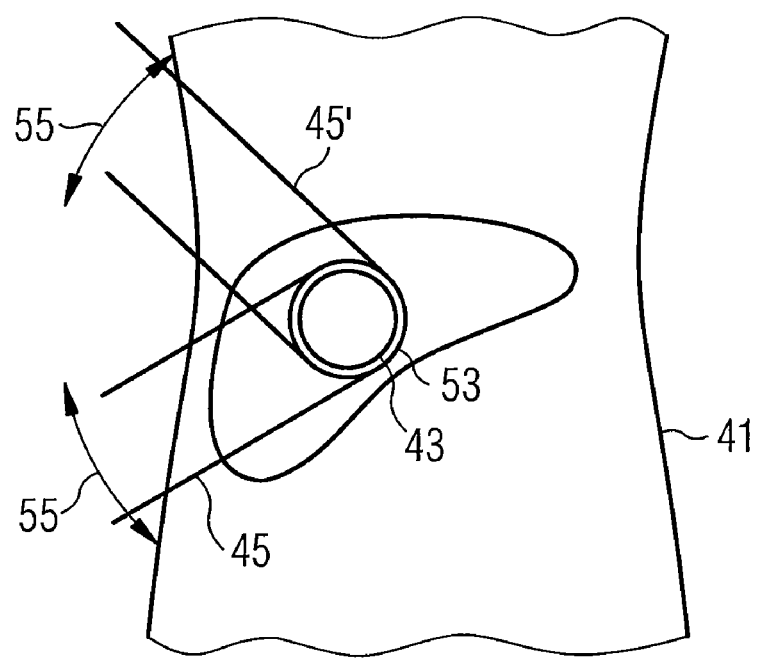
FIG. 4 shows a target volume to be irradiated with a plurality of planned irradiation fields.

The planning of an irradiating operation analogously to FIG. 3 is explained with reference to FIG. 4, with the difference that planning takes place in FIG. 4 with a plurality of irradiation fields 45, 45'. The representing of individual particle beams by target points has been dispensed with for clarity's sake.

Alternatively and/or additionally to the embodiments that were explained with reference to FIG. 3, for each irradiation field 45, 45' it will then be possible to ascertain a metric identifying in each case the density heterogeneity in one of the irradiation fields 45, 45'. The metrics may be used for determining a weighting of the irradiation fields 45, 45' among each other.

Figure 5:
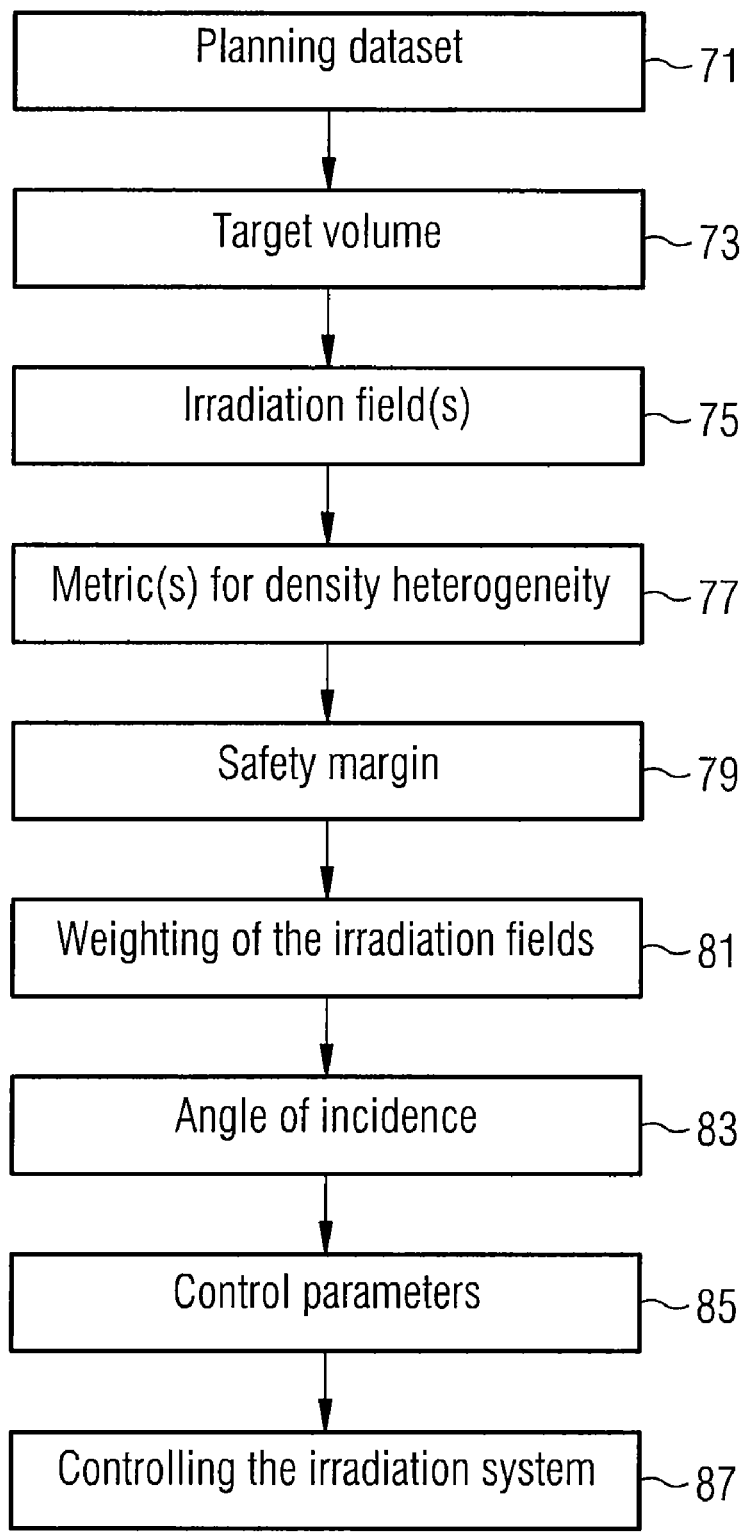
FIG. 5 illustrates one embodiment of a method for controlling an irradiation system.

FIG. 5 is a schematic overview of a method that may be performed according to one embodiment.

A planning dataset is first made available in which the object, which is to be irradiated, is imaged (act 71). The target volume that is to receive a specific dose is then determined in the (act 73). One or more irradiation fields are then established (act 75) for which a metric is in each case ascertained that identifies the density heterogeneity characterizing it/them (act 77). The metric is used to determine a weighting of the irradiation fields among each other (act 81) and/or a safety margin for individual irradiation fields (act 79). The angle of incidence of the irradiation field(s) may be selected as a function of the metric (act 83). Control parameters for controlling the system can be ascertained from the radiation treatment plan once a radiation treatment plan has been produced (act 85). The irradiation system is controlled using the ascertained control parameters for performing irradiating in accordance with the radiation treatment plan (act 87).

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A device for producing a radiation treatment plan, the device comprising:
    a computer unit having an input device and an output device, the computer unit being operable to:
        specify a dataset in which an object, which is to be irradiated, is represented,
        determine a target volume to be irradiated within the object,
        ascertain an index identifying a density heterogeneity for a region that will be struck by a planned treatment beam, and
        determine as a function of the ascertained index a safety margin for the target volume to be irradiated.

2. The device as claimed in claim 1, wherein the computer unit is operable to establish the irradiating of the target volume by a multiplicity of particle beams to be applied successively, the region including an area that will be struck by a plurality of the multiplicity of particle beams to be applied successively.

3. The device as claimed in claim 1, wherein the region includes an area situated in an entry channel of the planned treatment beam in front of the target volume in the beam direction.

4. The device as claimed in claim 1, wherein the region includes an entire area that will be struck by the planned treatment beam.

5. The device as claimed in claim 1, wherein the computer unit is operable to select an entry angle of the planned treatment beam as a function of the index.

6. The device as claimed in claim 1, wherein the computer unit is operable to check a dose distribution defined by the planned treatment beam for dose distribution robustness with respect to spatial imprecision in dose depositing.

7. A device for producing a radiation treatment plan, the device comprising a computer unit having an input device and an output device, the computer unit being operable to:
    specify a dataset in which an object, which is to be irradiated, is represented,
    determine a target volume that is to be irradiated within the object,
    specify at least two irradiation fields with which the target volume will be irradiated from in each case a different direction,
    ascertain for each of the at least two irradiation fields an index that identifies a density homogeneity for a region which will be struck during planned irradiating with the respective irradiating field, and
    determine a weighting for the at least two irradiation fields as a function of the index ascertained.

8. The device as claimed in claim 7, wherein the computer unit is operable to establish the irradiating of the target volume by a multiplicity of particle beams to be applied successively, the region including an area that will be struck by a plurality of the particle beams to be applied successively for the irradiation field.

9. The device as claimed in claim 7, wherein the region for one of the at least two irradiation fields includes an area that is situated in an entry channel of a treatment beam in front of the target volume in the treatment beam direction.

10. The device as claimed in claim 7, wherein the region for one of the at least two irradiation fields includes an entire area that will be struck by a treatment beam.

11. The device as claimed in claim 7, wherein the weighting, an entry angle and a safety margin are selected for at least one of the at least two irradiation fields as a function of the indices ascertained.

12. The device as claimed in claim 7, wherein the computer unit is operable to check a dose distribution defined by the planned irradiating for one of the at least two irradiation fields for dose distribution robustness with respect to spatial imprecision in dose depositing.

13. The device as claimed in claim 7, wherein an entry angle or a safety margin is selected for at least one of the at least two irradiation fields as a function of the indices ascertained.

14. A method for producing a radiation treatment plan, the method comprising:
    specifying a dataset in which an object to be irradiated is represented,
    determining a target volume to be irradiated within the object,
    ascertaining an index identifying a density heterogeneity for a region that will be struck by a planned treatment beam, and
    determining as a function of the ascertained index a safety margin for the target volume.

15. A method for producing a radiation treatment plan, the method comprising:
    specifying a dataset in which an object to be irradiated is represented,
    determining a target volume to be irradiated within the object, specifying at least two irradiation fields with which the target volume will be irradiated from in each case a different direction,
    ascertaining for each of the at least two irradiation fields an index that identifies a density homogeneity for a region which will be struck during planned irradiating with the respective irradiating field, and
    determining a weighting for the at least two irradiating fields as a function of the indices ascertained.

* * * * *